(12) United States Patent
Alliger

(10) Patent No.: US 10,329,363 B2
(45) Date of Patent: Jun. 25, 2019

(54) GROUP 6 TRANSITION METAL CATALYST COMPOUND AND USE THEREOF

(71) Applicant: ExxonMobil Chemical Patents Inc.

(72) Inventor: Glen E. Alliger, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/975,280

(22) Filed: Dec. 18, 2015

(65) Prior Publication Data

US 2016/0280820 A1    Sep. 29, 2016

Related U.S. Application Data

(60) Provisional application No. 62/136,774, filed on Mar. 23, 2015.

(51) Int. Cl.

| | |
|---|---|
| C08F 4/69 | (2006.01) |
| C08F 10/02 | (2006.01) |
| C08F 210/16 | (2006.01) |
| C07F 17/00 | (2006.01) |
| C08F 4/639 | (2006.01) |

(52) U.S. Cl.
CPC ............ C08F 210/16 (2013.01); C07F 17/00 (2013.01); C08F 4/69 (2013.01); C08F 4/63912 (2013.01); C08F 4/63916 (2013.01)

(58) Field of Classification Search
CPC .......... C08F 4/69; C08F 10/00; C08F 210/16; C07F 17/00
See application file for complete search history.

(56) References Cited

U.S. PATENT DOCUMENTS

| | | |
|---|---|---|
| 2,825,721 A | 3/1958 | Hogan et al. |
| 5,593,931 A | 1/1997 | Beach et al. |
| 2006/0094590 A1 | 5/2006 | McDaniel et al. |
| 2010/0267901 A1 | 10/2010 | Fantinel et al. |
| 2012/0059134 A1 | 3/2012 | Yang et al. |
| 2013/0225820 A1 | 8/2013 | Ding et al. |

FOREIGN PATENT DOCUMENTS

| | | |
|---|---|---|
| BE | 723775 | 5/1969 |
| CN | 102070732 | 5/2011 |
| DE | 197 10 615 | 9/1998 |
| EP | 0 742 046 | 11/1996 |
| JP | 2004/217568 | 8/2004 |
| WO | WO98/04570 | 2/1998 |
| WO | 01/02323 | 1/2001 |
| WO | 02/31001 | 4/2002 |
| WO | 2006/052232 | 5/2006 |
| WO | 2008/140175 | 11/2008 |
| WO | 2011/089017 | 7/2011 |
| WO | 2012/040147 | 3/2012 |

OTHER PUBLICATIONS

Baker, R.T. et al., "New (n—O5Me5)M(PR2)x Complexes (M=Ta, Mo, and W): Reversible P—H Bond Activation, sp3 C—H Bond Activation, and P—C Bond Formation," Organometallics, 1993, vol. 12, pp. 830-841.
Hocher, T. et al., "Phosphanylalkylcyclopentadienyl ligands: synthesis, molecular structures and catalytic properties of [{(n 5—C5H4) CMe2PHR}CrC12(PMe2Ph)] (R=Ph, tBu)," Polyhedron, 2004, vol. 23, pp. 1393-1399.
Liang, Y. et al., "*Constrained Geometry Chromium Catalysts for Olefin Polymerization*," Organometallics, 1996, vol. 15, pp. 5284-5286.
U.S. Appl. No. 62/012,047, filed Jun. 13, 2014, Alligar et al.
Dohring et al., "*Donor-Ligand-Substituted Cyclopentadienylchromium(III) Complexes: A New Class of Alkene Polymerization Catalyst. 1. Amino-Substituted Systems*," Organometallics, 2000, vol. 19, pp. 388-402.
Kurek et al., "*Mesoporous Silica Supported Multiple Single-Site Catalysts and Polyethylene Reactor Blends with Tailor-Made Trimodal and Ultra-Broad Molecular Weight Distributions*," Macromolecular Rapid Communications, 2010, vol. 31, pp. 1359-1363.
McDaniel, "*A Review of the Phillips Supported Chromium Catalyst and Its Commercial Use for Ethylene Polymerization*," Advances in Catalysis, 2010, vol. 53, pp. 123-606.

*Primary Examiner* — Caixia Lu

(57) ABSTRACT

This invention relates to a catalyst system comprising a half sandwich chromocene compound featuring a tethered P-donor, with an activator and optional supportation on silica which produces ethylene homopolymer or copolymer.

19 Claims, 1 Drawing Sheet

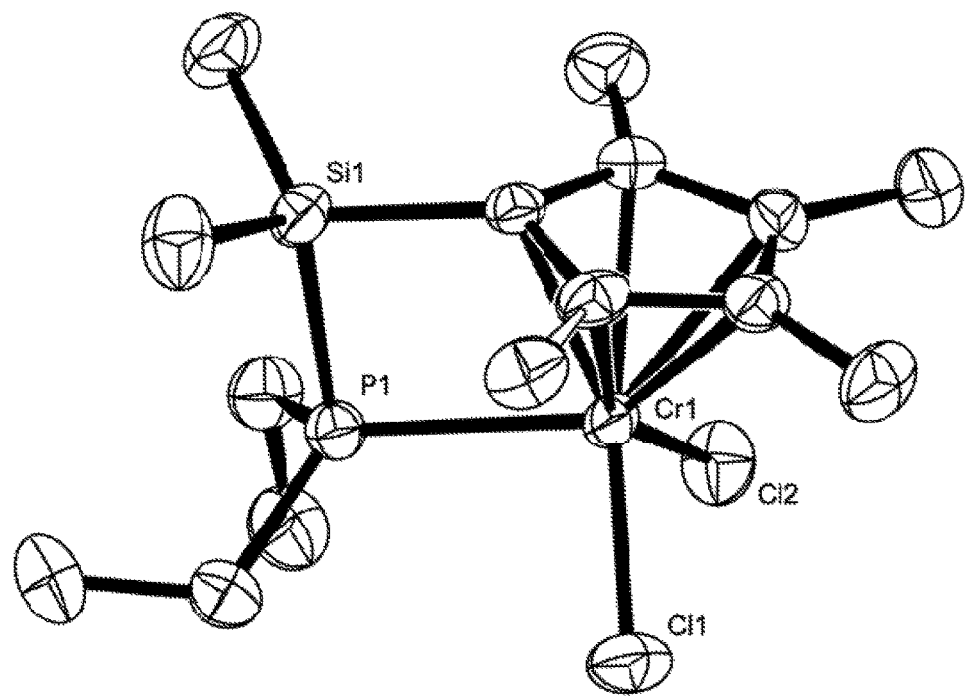

GROUP 6 TRANSITION METAL CATALYST COMPOUND AND USE THEREOF

CROSS REFERENCE TO RELATED APPLICATIONS

This invention claims priority to and the benefit of U.S. Ser. No. 62/136,774, filed Mar. 23, 2015.

FIELD OF THE INVENTION

This invention relates to catalyst systems comprising a chromium metallocene catalyst compound and their use to polymerize olefins.

BACKGROUND OF THE INVENTION

Chromium oxide, deposited directly onto silica, is an active ethylene polymerization catalyst, (see U.S. Pat. No. 2,825,721 and McDaniel, M. P., *A Review of the Phillips Supported Chromium Catalyst and Its Commercial Use for Ethylene Polymerization. Advances in Catalysis.*, Bruce, C. G.; Helmut, K., Eds. Academic Press: 2010; Vol. 53, 123-606) as is chromocene ($Cp_2Cr$) deposited on silica (see Karapinka, G. L. BE723775, 1968). Despite these discoveries being decades old, there is still much research to be done on chromium olefin polymerization catalysts. Specifically, discrete chromium(III) organometallic catalysts have received a lot of attention lately; such catalysts are of interest because the plastics they make may be useful to industry.

Half sandwich chromocenes are disclosed in DE 19710615; WO 2012/040147; US 2013/225820; US 2010/267901; and CN 102070732. , In particular, J. *Organometallics* 2000, 19, 388-402 (Dohring, A. et al.) discloses ethylene(cyclopentadienyl)(pyrrolidine)chromium dichloride.

Other references of interest include: US 2012/059134; *Macromol. Rapid Comm.* 2010, 31, 1359-1363 (d. Kurek, A, et al.); WO 2011/089017; WO 2006/052232; WO 2008/140175; and U.S. Ser. No. 62/012,047 filed Jun. 13, 2014.

There is still a need in the art for new and improved catalyst systems for the polymerization of olefins, in order to achieve specific polymer properties, such as impact resistance without negatively impacting the resulting polymer's processability properties.

It is therefore an object of the present invention to provide novel catalyst compounds, catalyst systems comprising such compounds, and processes for the polymerization of olefins using such compounds and systems.

SUMMARY OF THE INVENTION

This invention relates to a catalyst system comprising activator, optional support, catalyst compound represented by Formula I and a process to polymerize olefins (such as ethylene) with said catalyst system, where Formula I is:

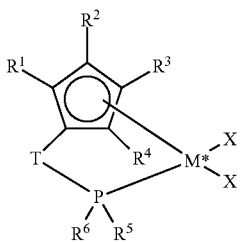

wherein:

T is a bridging group; P is phosphorus; M* is Cr, Mo, or W; each X, is independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's may form a part of a fused ring or a ring system), preferably each X is independently selected from halides and $C_1$ to $C_5$ alkyl groups, preferably each X is a chloride, bromide or a methyl group;

each $R^1$, $R^2$, $R^3$, and $R^4$ is independently, hydrogen, a $C_1$ to $C_{12}$ hydrocarbyl, a substituted $C_1$ to $C_{12}$ hydrocarbyl, a heteroatom, or substituted heteroatom group; and each $R^5$ and $R^6$ is, independently, a $C_1$ to $C_{12}$ hydrocarbyl, a substituted $C_1$ to $C_{12}$ hydrocarbyl, a heteroatom, or substituted heteroatom group, where the $R^5$ and $R^6$ groups may form a fused ring or multicenter fused ring system where the rings may be aromatic, partially saturated or saturated.

This invention relates to a method to polymerize olefins comprising contacting a catalyst compound with an activator and one or more monomers. This invention further relates to novel catalyst systems.

BRIEF DESCRIPTION OF THE FIGURES

FIG. 1 is the ORTEP drawing of a catalyst compound of this invention, i.e., $Me_4CpSiMe_2PEt_2]CrCl_2$.

DETAILED DESCRIPTION OF THE INVENTION

For the purposes of this invention and the claims thereto, the new numbering scheme for the Periodic Table Groups is used as described in CHEMICAL AND ENGINEERING NEWS, 63(5), pg. 27 (1985).

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

For the purposes of this invention, ethylene shall be considered an α-olefin.

For purposes of this invention and claims thereto, the term "substituted" means that a hydrogen group has been replaced with a heteroatom, or a heteroatom containing group. For example, a "substituted hydrocarbyl" is a radical made of carbon and hydrogen where at least one hydrogen is replaced by a heteroatom or heteroatom containing group.

As used herein, Mn is number average molecular weight, Mw is weight average molecular weight, and Mz is z average molecular weight, wt % is weight percent, and mol % is mole percent. Molecular weight distribution (MWD), also referred to as polydispersity, is defined to be Mw divided by Mn. Unless otherwise noted, all molecular weight units (e.g., Mw, Mn, Mz) are g/mol. The following abbreviations may be used herein: Me is methyl, Et is ethyl, Pr is propyl, cPR is cyclopropyl, nPr is n-propyl, iPr is isopropyl, Bu is butyl, nBu is normal butyl, iBu is isobutyl, sBu is sec-butyl, tBu is tert-butyl, Oct is octyl, Ph is phenyl, Bn is benzyl, MAO is methylalumoxane.

A "catalyst system" is the combination of at least one chromium metallocene catalyst compound (represented by Formula I), at least one activator, an optional co-activator, and, optionally a support material, such as silica. For the purposes of this invention and the claims thereto, when catalyst systems are described as comprising neutral stable forms of the components, it is well understood by one of ordinary skill in the art, that the ionic form of the component is the form that reacts with the monomers to produce polymers.

In the description herein, the metallocene catalyst may be described as a catalyst precursor, a pre-catalyst compound, metallocene catalyst compound, or a transition metal compound, and these terms are used interchangeably. A polymerization catalyst system is a catalyst system that can polymerize monomers to polymer. An "anionic ligand" is a negatively charged ligand which donates one or more pairs of electrons to a metal ion. A "cationic ligand" is a positively charged ligand which donates one or more pairs of electrons to a metal ion. A "neutral donor ligand" is a neutrally charged ligand which donates one or more pairs of electrons to a metal ion.

A metallocene catalyst is defined as an organometallic compound with at least one π-bound cyclopentadienyl moiety (or substituted cyclopentadienyl moiety) bound to a transition metal.

For purposes of this invention and claims thereto in relation to metallocene catalyst compounds, the term "substituted" means that a hydrogen group has been replaced with a hydrocarbyl group, a heteroatom, or a heteroatom containing group. For example, methyl cyclopentadiene (Cp) is a Cp group substituted with a methyl group.

Catalyst System

In a preferred embodiment, this invention relates to catalyst systems comprising activator(s), support(s), at least one catalyst compound represented by Formula I, where Formula I is:

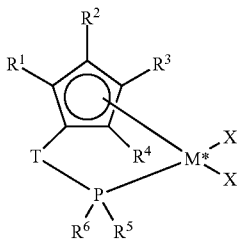

wherein:

T is a bridging group; P is phosphorus; M* is Cr, Mo, or W, preferably Cr; each X is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's may form a part of a fused ring or a ring system), preferably each X is independently selected from halides and $C_1$ to $C_5$ alkyl groups, preferably each X is a chloride, bromide or a methyl group; each $R^1$, $R^2$, $R^3$, and $R^4$ is, independently, a $C_1$ to $C_{12}$ hydrocarbyl, a substituted $C_1$ to $C_{12}$ hydrocarbyl, a heteroatom, or substituted heteroatom group; and each $R^5$ and $R^6$ is, independently, a $C_1$ to $C_{12}$ hydrocarbyl, a substituted $C_1$ to $C_{12}$ hydrocarbyl, a heteroatom, or substituted heteroatom group, where the $R^5$ and $R^6$ groups may form a fused ring or multicenter fused ring system where the rings may be aromatic, partially saturated or saturated.

In a preferred embodiment of the invention in any embodiment of any formula described herein, each $R^1$, $R^2$, $R^3$, and $R^4$ is, independently, hydrogen, methyl, ethyl, propyl, butyl, pentyl, hexyl, heptyl, octyl, nonyl, decyl, undecyl, docecyl, or an isomer thereof, Cl, Br, F, I, or Si, preferably methyl, ethyl, propyl, butyl or an isomer thereof.

In a preferred embodiment of the invention, each $R^5$ and $R^6$, is, independently, methyl, ethyl, propyl, butyl, pentyl, hexyl, heptyl, octyl, nonyl, decyl, undecyl, docecyl, or an isomer thereof, Cl, Br, F, I, or Si.

In a preferred embodiment of the invention in any embodiment of any formula described herein, the $R^5$ and $R^6$ groups form a 3 to 24 membered fused ring with the phosphorus atom, where the rings may be aromatic, partially saturated or saturated, preferably saturated. In an embodiment, the ring(s) have 3 to 20, alternately 4 to 18, alternately 5 to 15, alternately 6 to 12. , Useful $P(R^5)(R^6)$ fragments include: diethylphosphino, diphenylphosphino, di-t-butylphosphino, dicyclohexylphosphino, di-p-tolylphosphino, or substituted versions thereof, where the substituents are alkyl, aryl, silyl, and or halide groups.

Useful $P(R^5)(R^6)$ fragments are neutral donor ligands. A neutral donor ligand is defined as one that, in its uncoordinated state, bears a formal charge of zero. Useful $P(R^1)(R^2)$ fragments are not anionic ligands and are not cationic ligands.

In a preferred embodiment of the invention in any embodiment of any formula described herein, T is a bridging group and is represented by $R'_2C$, $R'_2Si$, $R'_2Ge$, $R'_2CCR'_2$, $R'_2CCR'_2CR'_2$, $R'_2CCR'_2CR'_2CR'_2$, $R'C=CR'$, $R'C=CR'CR'_2$, $R'_2CCR'=CR'CR'_2$, $R'C=CR'CR'=CR'$, $R'C=CR'CR'_2CR'_2$, $R'_2CSiR'_2$, $R'_2SiSiR'_2$, $R_2CSiR'_2CR'_2$, $R'_2SiCR'_2SiR'_2$, $R'C=CR'SiR'_2$, $R'_2CGeR'_2$, $R'_2GeGeR'_2$, $R'_2CGeR'_2CR'_2$, $R'_2GeCR'_2GeR'_2$, $R'_2SiGeR'_2$, $R'C=CR'GeR'_2$, $R'B$, $R'_2C-BR'$, $R'_2C-BR'-CR'_2$, $R'_2C-O-CR'_2$, $R'_2CR'_2C-O-CR'_2CR'_2$, $R'_2C-O-CR'_2CR'_2$, $R'_2C-O-CR'=CR'$, $R'_2C-S-CR'_2$, $R'_2CR'_2C-S-CR'_2CR'_2$, $R'_2C-S-CR'_2CR'_2$, $R'_2C-S-CR'=CR'$, $R'_2C-Se-CR'_2$, $R'_2CR'_2C-Se-CR'_2CR'_2$, $R'_2C-Se-CR_2CR'_2$, $R'_2C-Se-CR'=CR'$, $R'_2C-N=CR'$, $R'_2C-NR'-CR'_2$, $R'_2C-NR'-CR'_2CR'_2$, $R'_2C-NR'-CR'=CR'$, $R'_2CR'_2C-NR'-CR'_2CR'_2$, $R'_2C-P=CR'$, or $R'_2C-PR'-CR'_2$ where each R' is, independently, hydrogen or a $C_1$ to $C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent. Preferably, T is a bridging group comprising carbon or silica, such as dialkylsilyl, preferably T is selected from $CH_2$, $CH_2CH_2$, $C(CH_3)_2$, $SiMe_2$, $SiPh_2$, SiMePh, silylcyclobutyl ($Si(CH_2)_3$), $(Ph)_2C$, $(p\text{-}(Et)_3SiPh)_2C$, and cyclopentasilylene ($Si(CH_2)_4$).

In a preferred embodiment of the invention in any embodiment of any formula described herein, T is represented by the formula $R_2{}^aJ$, where J is C, Si, or Ge, and each $R^a$ is, independently, hydrogen, halogen, $C_1$ to $C_{20}$ hydrocarbyl or a $C_1$ to $C_{20}$ substituted hydrocarbyl, and two $R^a$ can form a cyclic structure including aromatic, partially saturated, or saturated cyclic or fused ring system.

In a preferred embodiment of the invention in any embodiment of any formula described herein, T is represented by the formula, $(R^*{}_2G)_g$, where each G is C, Si, or Ge, g is 1 or 2, and each $R^*$ is, independently, hydrogen, halogen, $C_1$ to $C_{20}$ hydrocarbyl or a $C_1$ to $C_{20}$ substituted hydrocarbyl, and two or more $R^*$ can form a cyclic structure including aromatic, partially saturated, or saturated cyclic or fused ring system, preferably T is $CH_2$, $CH_2CH_2$, $C(CH_3)_2$, $SiMe_2$, $SiPh_2$, SiMePh, $Si(CH_2)_3$, $Si(CH_2)_4$, $Si(CH_2)_5$ or $CPh_2$.

In an embodiment of the invention in any embodiment of any formula described herein, $M^*$ is Cr.

In a preferred embodiment of the invention in any embodiment of any formula described herein, $R^1$, $R^2$, $R^3$, and $R^4$ is methyl Me.

Catalyst compounds represented by Formula I that are particularly useful in this invention include one or more of: tetramethyl(diethylphosphinodimethylsilyl)cyclopentadienylchromium(III) dichloride, tetramethyl(diphenylphosphinodimethylsilyl)cyclopentadienylchromium(III) dichloride, tetramethyl(di-p-tolylphosphinodimethylsilyl)cyclopentadienylchromium(III) dichloride, tetramethyl(dicyclohexylphosphinodimethylsilyl)cyclopentadienylchromium(III) dichloride, and tetramethyl(di-t-butylphosphinodimethylsilyl)cyclopentadienylchromium(III) dichloride.

Methods to Prepare the Catalyst Compounds

Useful catalyst compounds represented by Formula I can be prepared by means known in the art, such as by 1) lithiation of a secondary phosphine, 2) addition of an electrophilic silyl Cp source, 3) deprotonation of the formed ligand, and 4) addition of a chromium salt. The scheme below is illustrative:

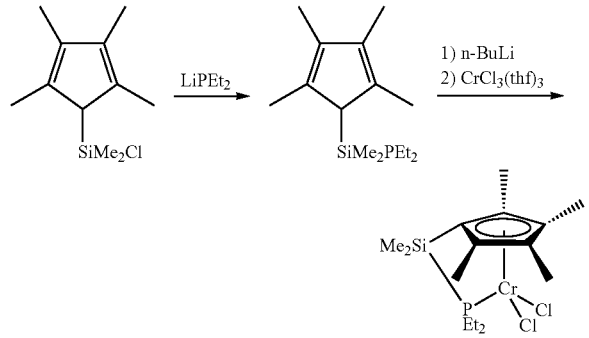

Activators

The terms "cocatalyst" and "activator" are used herein interchangeably and are defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract a reactive, σ-bound, metal ligand making the metal complex cationic and providing a charge-balancing noncoordinating or weakly coordinating anion.

In one embodiment, alumoxane activators are utilized as an activator in the catalyst composition. Alumoxanes are generally oligomeric compounds containing —Al($R^1$)—O— sub-units, where $R^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methyl alumoxane (MMAO) cocatalyst type 3A (commercially available from Akzo Chemicals, Inc. under the tradename Modified Methylalumoxane type 3A, covered under patent number U.S. Pat. No. 5,041,584).

When the activator is an alumoxane (modified or unmodified), some embodiments select the maximum amount of activator typically at up to a 5000-fold molar excess Al/M over the catalyst compound (per metal catalytic site). The minimum activator-to-catalyst-compound is a 1:1 molar ratio. Alternate preferred ranges include from 1:1 to 500:1, alternately from 1:1 to 200:1, alternately from 1:1 to 100:1, or alternately from 1:1 to 50:1.

In an alternate embodiment, little or no alumoxane is used in the polymerization processes described herein. Preferably, alumoxane is present at zero mole %; alternately the alumoxane is present at a molar ratio of aluminum to catalyst compound transition metal less than 500:1, preferably less than 300:1, preferably less than 100:1, preferably less than 1:1.

The term "non-coordinating anion" (NCA) means an anion which either does not coordinate to a cation or which is only weakly coordinated to a cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri(n-butyl)ammonium tetrakis(pentafluorophenyl)borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium, and indium, or mixtures thereof. The three substituent groups are each independently selected from alkyls, alkenyls, halogens, substituted alkyls, aryls, arylhalides, alkoxy, and halides. Preferably, the three groups are independently selected from halogen, mono or multicyclic (including halosubstituted) aryls, alkyls, and alkenyl compounds, and mixtures thereof; preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl, or mixtures thereof. Even more preferably, the three groups are halogenated, preferably fluorinated, aryl groups. A preferred neutral stoichiometric activator is tris perfluorophenyl boron or tris perfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in EP 0 570 982 A; EP 0 520 732 A; EP 0 495 375 A; EP 0 500 944 B1; EP 0 277 003 A; EP 0 277 004 A; U.S. Pat. Nos. 5,153,157; 5,198,401; 5,066,741; 5,206,197; 5,241,025; 5,384,299; 5,502,124; and U.S. Ser. No. 08/285,380, filed Aug. 3, 1994; all of which are herein fully incorporated by reference.

Preferred compounds useful as an activator in the process of this invention comprise a cation, which is preferably a Bronsted acid capable of donating a proton, and a compatible non-coordinating anion which anion is relatively large (bulky), capable of stabilizing the active catalyst species (the Group 4 cation) which is formed when the two compounds are combined and said anion will be sufficiently labile to be displaced by olefinic, diolefinic and acetylenically unsaturated substrates or other neutral Lewis bases, such as ethers, amines, and the like. Two classes of useful compatible non-coordinating anions have been disclosed in EP 0 277 003 A1 and EP 0 277 004 A1: 1) anionic coordination complexes comprising a plurality of lipophilic radicals covalently coordinated to and shielding a central charge-bearing metal or metalloid core; and 2) anions comprising a plurality of boron atoms such as carboranes, metallacarboranes, and boranes.

In a preferred embodiment, the stoichiometric activators include a cation and an anion component, and are preferably represented by the following formula (II):

$$(Z)_d^+(A^{d-}) \tag{II}$$

wherein Z is (L-H) or a reducible Lewis Acid, L is an neutral Lewis base; H is hydrogen; (L-H)+ is a Bronsted acid; $A^{d-}$ is a non-coordinating anion having the charge d−; and d is an integer from 1 to 3.

When Z is (L-H) such that the cation component is $(L-H)_d^+$, the cation component may include Bronsted acids such as protonated Lewis bases capable of protonating a moiety, such as an alkyl or aryl, from the bulky ligand metallocene containing transition metal catalyst precursor, resulting in a cationic transition metal species. Preferably, the activating cation $(L-H)_d^+$ is a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether, diethyl ether, tetrahydrofuran, and dioxane, sulfoniums from thioethers, such as diethyl thioethers and tetrahydrothiophene, and mixtures thereof.

When Z is a reducible Lewis acid, it is preferably represented by the formula: $(Ar_3C^+)$, where Ar is aryl or aryl substituted with a heteroatom, a $C_1$ to $C_{40}$ hydrocarbyl, or a substituted C1 to C40 hydrocarbyl, preferably the reducible Lewis acid is represented by the formula: $(Ph_3C^+)$, where Ph is phenyl or phenyl substituted with a heteroatom, a $C_1$ to $C_{40}$ hydrocarbyl, or a substituted C1 to C40 hydrocarbyl. In a preferred embodiment, the reducible Lewis acid is triphenyl carbenium.

The anion component $A^{d-}$ includes those having the formula $[M^{k+}Q_n]^{d-}$ wherein k is 1, 2, or 3; n is 1, 2, 3, 4, 5, or 6, preferably 3, 4, 5 or 6; n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide, and two Q groups may form a ring structure. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ components also include diboron compounds as disclosed in U.S. Pat. No. 5,447,895, which is fully incorporated herein by reference.

In a preferred embodiment, this invention relates to a method to polymerize olefins comprising contacting olefins (preferably ethylene and/or propylene) with the catalyst compound and a boron containing NCA activator represented by the formula (14):

$$Z_d^+(A^{d-}) \tag{14}$$

where: Z is (L-H) or a reducible Lewis acid; L is an neutral Lewis base (as further described above); H is hydrogen; (L-H) is a Bronsted acid (as further described above); $A^{d-}$ is a boron containing non-coordinating anion having the charge d− (as further described above); d is 1, 2, or 3.

In a preferred embodiment in any NCA's represented by Formula 14 described above, the reducible Lewis acid is represented by the formula: $(Ar_3C^+)$, where Ar is aryl or aryl substituted with a heteroatom, a $C_1$ to $C_{40}$ hydrocarbyl, or a substituted C1 to C40 hydrocarbyl, preferably the reducible Lewis acid is represented by the formula: $(Ph_3C^+)$, where Ph is phenyl or phenyl substituted with a heteroatom, a $C_1$ to $C_{40}$ hydrocarbyl, or a substituted C1 to C40 hydrocarbyl.

In a preferred embodiment in any of the NCA's represented by Formula 14 described above, $Z_d^+$ is represented by the formula: $(L-H)_d^+$, wherein L is an neutral Lewis base; H is hydrogen; (L-H) is a Bronsted acid; and d is 1, 2, or 3, preferably $(L-H)_d^+$ is a Bronsted acid selected from ammoniums, oxoniums, phosphoniums, silyliums, and mixtures thereof.

In a preferred embodiment in any of the NCA's represented by Formula 14 described above, the anion component $A^{d-}$ is represented by the formula $[M^{*k*}+Q^*_{n^*}]^{d^*-}$ wherein k* is 1, 2, or 3; n* is 1, 2, 3, 4, 5, or 6 (preferably 1, 2, 3, or 4); n*−k*=d*; M* is boron; and Q* is independently selected from hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q* having up to 20 carbon atoms with the proviso that in not more than 1 occurrence is Q* a halide.

This invention also relates to a method to polymerize olefins comprising contacting olefins (such as ethylene and or propylene) with the catalyst compound, an optional chain transfer agent and an NCA activator represented by the formula (I):

$$R_nM^{**}(ArNHal)_{4-n} \tag{I}$$

wherein:

R is a monoanionic ligand; M** is a Group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3., Typically, the NCA comprising an anion of Formula I also comprises a suitable cation that is essentially non-interfering with the ionic catalyst complexes formed with the transition metal compounds, preferably the cation is $Z_d^+$ as described above.

In a preferred embodiment in any of the NCA's comprising an anion represented by Formula I described above, R is selected from the group consisting of substituted or unsubstituted $C_1$ to $C_{30}$ hydrocarbyl aliphatic or aromatic groups, where substituted means that at least one hydrogen on a carbon atom is replaced with a hydrocarbyl, halide, halocarbyl, hydrocarbyl or halocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means $C_4$ to $C_{20}$ hydrocarbyl groups; —$SR^1$, —$NR^2{}_2$, and —$PR^3{}_2$, where each $R^1$, $R^2$, or $R^3$ is independently a substituted or unsubstituted hydrocarbyl as defined above; or a $C_1$ to $C_{30}$ hydrocarbyl substituted organometalloid.

In a preferred embodiment in any of the NCA's comprising an anion represented by Formula I described above, the NCA also comprises cation comprising a reducible Lewis acid represented by the formula: $(Ar_3C^+)$, where Ar is aryl or aryl substituted with a heteroatom, a $C_1$ to $C_{40}$ hydrocarbyl, or a substituted C1 to C40 hydrocarbyl, preferably the reducible Lewis acid represented by the formula: $(Ph_3C^+)$, where Ph is phenyl or phenyl substituted with a heteroatom, a $C_1$ to $C_{40}$ hydrocarbyl, or a substituted $C_1$ to $C_{40}$ hydrocarbyl.

In a preferred embodiment in any of the NCA's comprising an anion represented by Formula I described above, the NCA also comprises a cation represented by the formula, $(L\text{-}H)_d^+$, wherein L is an neutral Lewis base; H is hydrogen; (L-H) is a Bronsted acid; and d is 1, 2, or 3, preferably $(L\text{-}H)_d^+$ is a Bronsted acid selected from ammoniums, oxoniums, phosphoniums, syliums, and mixtures thereof.

Further examples of useful activators include those disclosed in U.S. Pat. Nos. 7,297,653 and 7,799,879.

Another activator useful herein comprises a salt of a cationic oxidizing agent and a noncoordinating, compatible anion represented by the formula (16):

$$(OX^{e+})_d(A^{d-})_e \tag{16}$$

wherein $OX^{e+}$ is a cationic oxidizing agent having a charge of e+; e is 1, 2, or 3; d is 1, 2 or 3; and $A^{d-}$ is a non-coordinating anion having the charge of d− (as further described above). Examples of cationic oxidizing agents include: ferrocenium, hydrocarbyl-substituted ferrocenium, $Ag^+$, or $Pb^{+2}$. Preferred embodiments of $A^{d-}$ include tetrakis (pentafluorophenyl)borate.

In another embodiment, the amidinate catalyst compounds and optional CTA's described herein can be used with Bulky activators. A "Bulky activator" as used herein refers to anionic activators represented by the formula:

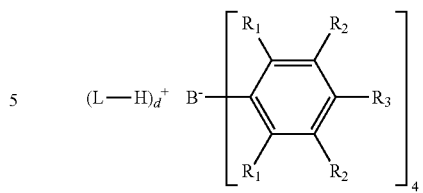

wherein:

each $R_1$ is, independently, a halide, preferably a fluoride;

each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_2$ is a fluoride or a perfluorinated phenyl group);

each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring);

L is an neutral Lewis base; $(L\text{-}H)^+$ is a Bronsted acid; d is 1, 2, or 3;

wherein the anion has a molecular weight of greater than 1020 g/mol; and wherein at least three of the substituents on the B atom each have a molecular volume of greater than 250 cubic Å, alternately greater than 300 cubic Å, or alternately greater than 500 cubic Å.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple "Back of the Envelope" Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: $MV=8.3V_s$, where $V_s$ is the scaled volume. $V_s$ is the sum of the relative volumes of the constituent atoms, and is calculated from the molecular formula of the substituent using the following table of relative volumes. For fused rings, the $V_s$ is decreased by 7.5% per fused ring.

| Element | Relative Volume |
| --- | --- |
| H | 1 |
| 1st short period, Li to F | 2 |
| 2nd short period, Na to Cl | 4 |
| 1st long period, K to Br | 5 |
| 2nd long period, Rb to I | 7.5 |
| 3rd long period, Cs to Bi | 9 |

Exemplary bulky substituents of activators suitable herein and their respective scaled volumes and molecular volumes are shown in the table below. The dashed bonds indicate binding to boron, as in the general formula above.

| Activator | Structure of boron substituents | Molecular Formula of each substituent | $V_S$ | MV Per subst. (Å³) | Total MV (Å³) |
|---|---|---|---|---|---|
| Dimethylanilinium tetrakis(perfluoronaphthyl)borate | [perfluoronaphthyl structure] | $C_{10}F_7$ | 34 | 261 | 1044 |
| Dimethylanilinium tetrakis(perfluorobiphenyl)borate | [perfluorobiphenyl structure] | $C_{12}F_9$ | 42 | 349 | 1396 |
| [4-tButyl-PhNMe₂H][(C₆F₃(C₆F₅)₂)₄B] | [perfluoroterphenyl structure] | $C_{18}F_{13}$ | 62 | 515 | 2060 |

Exemplary bulky activators useful in catalyst systems herein include: trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, [4-t-butyl-PhNMe₂H][(C₆F₃(C₆F₅)₂)₄B], and the types disclosed in U.S. Pat. No. 7,297,653.

Illustrative, but not limiting, examples of boron compounds which may be used as an activator in the processes of this invention are: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium)tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl) ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, and dialkyl ammonium salts, such as: di-(i-propyl) ammonium tetrakis(pentafluorophenyl)borate, and dicyclohexylammonium tetrakis(pentafluorophenyl)borate; and additional tri-substituted phosphonium salts, such as tri(o-tolyl)phosphonium tetrakis(pentafluorophenyl)borate, and tri(2,6-dimethylphenyl)phosphonium tetrakis(pentafluorophenyl)borate.

Preferred activators include N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, $[Ph_3C^+][B(C_6F_5)_4^-]$, $Me_3NH^+][B(C_6F_5)_4^-]$; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl)borate, triphenylcarbenium tetrakis(perfluoronaphthyl)borate, triphenylcarbenium tetrakis(perfluorobiphenyl)borate, or triphenylcarbenium tetrakis(3,5-bis(trifluoromethyl)phenyl)borate).

In another embodiment, the activator comprises one or more of trialkylammonium tetrakis(pentafluorophenyl)borate, N,N-dialkylanilinium tetrakis(pentafluorophenyl)borate, N,N-dimethyl-(2,4,6-trimethylanilinium)tetrakis(pentafluorophenyl)borate, trialkylammonium tetrakis-(2,3,4,6-tetrafluorophenyl)borate, N,N-dialkylanilinium tetrakis-(2,3,4,6-tetrafluorophenyl)borate, trialkylammonium tetrakis(perfluoronaphthyl)borate, N,N-dialkylanilinium tetrakis(perfluoronaphthyl)borate, trialkylammonium tetrakis(perfluorobiphenyl)borate, N,N-dialkylanilinium tetrakis(perfluorobiphenyl)borate, trialkylammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl)phenyl)borate, di-(i-propyl)ammonium tetrakis(pentafluorophenyl)borate, (where alkyl is methyl, ethyl, propyl, n-butyl, sec-butyl, or t-butyl).

In a preferred embodiment, any of the activators described herein may be mixed together before or after combination with the catalyst compound, preferably before being mixed with the catalyst compound.

In some embodiments, two NCA activators may be used in the polymerization and the molar ratio of the first NCA activator to the second NCA activator can be any ratio. In some embodiments, the molar ratio of the first NCA activator to the second NCA activator is 0.01:1 to 10,000:1, preferably 0.1:1 to 1000:1, preferably 1:1 to 100:1.

Further, the typical activator-to-catalyst ratio, e.g., all NCA activators-to-catalyst ratio is a 1:1 molar ratio. Alternate preferred ranges include from 0.1:1 to 100:1, alternately from 0.5:1 to 200:1, alternately from 1:1 to 500:1 alternately from 1:1 to 1000:1. , A particularly useful range is from 0.5:1 to 10:1, preferably 1:1 to 5:1.

It is also within the scope of this invention that the catalyst compounds can be combined with combinations of alumoxanes and NCA's (see for example, U.S. Pat. Nos. 5,153,157; 5,453,410; EP 0 573 120 B1; WO 94/07928; and WO 95/14044 which discuss the use of an alumoxane in combination with an ionizing activator).

Optional Scavengers or Co-Activators

In addition to these activator compounds, scavengers or co-activators may be used. Aluminum alkyl or organoaluminum compounds which may be utilized as scavengers or co-activators include, for example, trimethylaluminum, triethylaluminum, triisobutylaluminum, tri-n-hexylaluminum, tri-n-octylaluminum, and diethyl zinc.

Optional Support Materials

In embodiments herein, the catalyst system may comprise an inert support material. Preferably, the supported material is a porous support material, for example, talc and inorganic oxides. Other support materials include zeolites, clays, organoclays, or any other organic or inorganic support material and the like, or mixtures thereof.

Preferably, the support material is an inorganic oxide in a finely divided form. Suitable inorganic oxide materials for use in metallocene catalyst systems herein include Groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be employed, for example, finely divided functionalized polyolefins, such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. Preferred support materials include $Al_2O_3$, $ZrO_2$, $SiO_2$, and combinations thereof, more preferably $SiO_2$, $Al_2O_3$, or $SiO_2/Al_2O_3$.

It is preferred that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 μm. More preferably, the surface area of the support material is from about 50 to about 500 $m^2/g$, pore volume of from about 0.5 to about 3.5 cc/g and average particle size of from about 10 to about 200 μm. Most preferably the surface area of the support material is in the range is from about 100 to about 400 $m^2/g$, pore volume from about 0.8 to about 3.0 cc/g and average particle size is from about 5 to about 100 μm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 $m^2/gm$; pore volume of 1.65 $cm^3/gm$). Preferred silicas are marketed under the tradenames of DAVISON 952 or DAVISON 955 by the Davison Chemical Division of W.R. Grace and Company. In other embodiments, DAVISON 948 is used.

The support material should be dry, that is, free of absorbed water. Drying of the support material can be effected by heating or calcining at about 100° C. to about 1000° C., preferably at least about 600° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours. The calcined support material must have at least some reactive hydroxyl (OH) groups to produce supported catalyst systems of this invention. The calcined support material is then contacted with at least one polymerization catalyst comprising at least one metallocene compound and an activator.

The support material, having reactive surface groups, typically hydroxyl groups, is slurried in a non-polar solvent and the resulting slurry is contacted with a solution of a metallocene compound and an activator. In some embodiments, the slurry of the support material is first contacted with the activator for a period of time in the range of from about 0.5 hours to about 24 hours, from about 2 hours to about 16 hours, or from about 4 hours to about 8 hours. The solution of the metallocene compound is then contacted with the isolated support/activator. In some embodiments, the supported catalyst system is generated in situ. In alternate embodiment, the slurry of the support material is first contacted with the catalyst compound for a period of time in the range of from about 0.5 hours to about 24 hours, from about 2 hours to about 16 hours, or from about 4 hours to about 8 hours. The slurry of the supported metallocene compound is then contacted with the activator solution.

The mixture of the metallocene, activator and support is heated to about 0° C. to about 70° C., preferably to about 23° C. to about 60° C., preferably at room temperature. Contact times typically range from about 0.5 hours to about 24 hours, from about 2 hours to about 16 hours, or from about 4 hours to about 8 hours.

Suitable non-polar solvents are materials in which all of the reactants used herein, i.e., the activator, and the metallocene compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

Polymerization Processes

In embodiments herein, the invention relates to polymerization processes where monomer (such as ethylene or propylene), and optionally comonomer, are contacted with a catalyst compound as described above and an activator. The catalyst compound and activator may be combined in any order, and are combined typically prior to contacting with the monomer.

Monomers useful herein include substituted or unsubstituted $C_2$ to $C_{40}$ alpha olefins, preferably $C_2$ to $C_{20}$ alpha olefins, preferably $C_2$ to $C_{12}$ alpha olefins, preferably ethylene, propylene, butene, pentene, hexene, heptene, octene, nonene, decene, undecene, dodecene and isomers thereof. In a preferred embodiment of the invention, the monomer comprises propylene and an optional comonomers comprising one or more ethylene or $C_4$ to $C_{40}$ olefins, preferably $C_4$ to $C_{20}$ olefins, or preferably $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups. In another preferred embodiment, the monomer comprises ethylene and an optional comonomers comprising one or more $C_3$ to $C_{40}$ olefins, preferably $C_4$ to $C_{20}$ olefins, or preferably $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene.

In a preferred embodiment, one or more dienes are present in the polymer produced herein at up to 10 wt %, preferably at 0.00001 to 1.0 wt %, preferably 0.002 to 0.5 wt %, even more preferably 0.003 to 0.2 wt %, based upon the total weight of the composition. In some embodiments, 500 ppm or less of diene is added to the polymerization, preferably 400 ppm or less, preferably or 300 ppm or less. In other embodiments, at least 50 ppm of diene is added to the polymerization, or 100 ppm or more, or 150 ppm or more.

Preferred diolefin monomers useful in this invention include any hydrocarbon structure, preferably $C_4$ to $C_{30}$, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e., di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

Polymerization processes of this invention can be carried out in any manner known in the art. Any suspension, homogeneous, bulk, solution, slurry, or gas phase polymerization process known in the art can be used. Such processes can be run in a batch, semi-batch, or continuous mode. Homogeneous polymerization processes and slurry processes are preferred. (A homogeneous polymerization process is defined to be a process where at least 90 wt % of the product is soluble in the reaction media.) A bulk homogeneous process is particularly preferred. (A bulk process is defined to be a process where monomer concentration in all feeds to the reactor is 70 volume % or more.) Alternately, no solvent or diluent is present or added in the reaction medium, (except for the small amounts used as the carrier for the catalyst system or other additives, or amounts typically found with the monomer; e.g., propane in propylene). In another embodiment, the process is a slurry process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt % based upon the weight of the solvents.

In a preferred embodiment, the feed concentration of the monomers and comonomers for the polymerization is 60 vol % solvent or less, preferably 40 vol % or less, or preferably 20 vol % or less, based on the total volume of the feedstream. Conveniently, the polymerization may be run in a bulk process.

Preferred polymerizations can be run at any temperature and/or pressure suitable to obtain the desired ethylene polymers. Typical temperatures and/or pressures include a temperature in the range of from about 0° C. to about 300° C., preferably about 20° C. to about 200° C., preferably about 35° C. to about 150° C., preferably from about 40° C. to about 120° C., preferably from about 45° C. to about 80° C.; and at a pressure in the range of from about 0.35 MPa to about 10 MPa, preferably from about 0.45 MPa to about 6 MPa, or preferably from about 0.5 MPa to about 4 MPa.

In a typical polymerization, the run time of the reaction is up to 300 minutes, preferably in the range of from about 5 to 250 minutes, or preferably from about 10 to 120 minutes.

In some embodiments, hydrogen is present in the polymerization reactor at a partial pressure of 0.001 to 50 psig (0.007 to 345 kPa), preferably from 0.01 to 25 psig (0.07 to 172 kPa), more preferably 0.1 to 10 psig (0.7 to 70 kPa).

In an alternate embodiment, the activity of the catalyst system is at least 50 g/mmol/hour, preferably 500 or more g/mmol/hour, preferably 5000 or more g/mmol/hr, preferably 50,000 or more g/mmol/hr. In an alternate embodiment, the conversion of olefin monomer is at least 10%, based upon polymer yield and the weight of the monomer entering the reaction zone, preferably 20% or more, preferably 30% or more, preferably 50% or more, preferably 80% or more.

In a preferred embodiment, little or no alumoxane is used in the process to produce the polymers. Preferably, alumoxane is present at zero mol %, alternately the alumoxane is present at a molar ratio of aluminum to transition metal less than 500:1, preferably less than 300:1, preferably less than 100:1, preferably less than 1:1.

In a preferred embodiment, little or no scavenger is used in the process to produce the ethylene polymer. Preferably, scavenger (such as tri alkyl aluminum) is present at zero mol %, alternately the scavenger is present at a molar ratio of scavenger metal to transition metal of less than 100:1, preferably less than 50:1, preferably less than 15:1, preferably less than 10:1.

In a preferred embodiment, the polymerization: 1) is conducted at temperatures of 0 to 300° C. (preferably 25 to 150° C., preferably 40 to 120° C., preferably 45 to 80° C.); 2) is conducted at a pressure of atmospheric pressure to 10 MPa (preferably 0.35 to 10 MPa, preferably from 0.45 to 6 MPa, preferably from 0.5 to 4 MPa); 3) is conducted in an aliphatic hydrocarbon solvent (such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof; preferably where aromatics are preferably present in the solvent at less than 1 wt %, preferably less than 0.5 wt %, preferably at 0 wt % based upon the weight of the solvents); 4) wherein the catalyst system used in the polymerization comprises less than 0.5 mol %, preferably 0 mol % alumoxane, alternately the alumoxane is present at a molar ratio of aluminum to transition metal less than 500:1, preferably less than 300:1, preferably less than 100:1, preferably less than 1:1; 5) the polymerization preferably occurs in one reaction zone; 6) optionally scavengers (such as trialkyl aluminum compounds) are absent (e.g., present at zero mol %, alternately the scavenger is present at a molar ratio of scavenger metal to transition metal of less than 100:1, preferably less than 50:1, preferably less than 15:1, preferably less than 10:1); and 7) optionally hydrogen is present in the polymerization reactor at a partial pressure of 0.001 to 50 psig (0.007 to 345 kPa) (preferably from 0.01 to 25 psig (0.07 to 172 kPa), more preferably 0.1 to 10 psig (0.7 to 70 kPa)). In a preferred embodiment, the catalyst system used in the polymerization comprises no more than one catalyst compound. A "reaction zone" also referred to as a "polymerization zone" is a vessel where polymerization takes place, for example a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In a preferred embodiment, the polymerization occurs in one reaction zone.

Other additives may also be used in the polymerization, as desired, such as one or more scavengers, promoters, modifiers, chain transfer agents (such as diethyl zinc), reducing agents, oxidizing agents, hydrogen, aluminum alkyls, or silanes.

Polyolefin Products

This invention also relates to compositions of matter produced by the methods described herein.

Likewise, the process of this invention produces olefin polymers, preferably polyethylene and polypropylene homopolymers and copolymers. In a preferred embodiment, the polymers produced herein are homopolymers of ethylene or are copolymers of ethylene preferably having from 0 to 25 mole % (alternately from 0.5 to 20 mole %, alternately from 1 to 15 mole %, preferably from 3 to 10 mole %) of one or more $C_3$ to $C_{20}$ olefin comonomer (preferably $C_3$ to $C_{12}$ alpha-olefin, preferably propylene, butene, hexene, octene, decene, dodecene, preferably propylene, butene, hexene, octene), or are copolymers of propylene preferably having from 0 to 25 mole % (alternately from 0.5 to 20 mole %, alternately from 1 to 15 mole %, preferably from 3 to 10 mole %) of one or more of $C_2$ or $C_4$ to $C_{20}$ olefin comonomer (preferably ethylene or $C_4$ to $C_{12}$ alpha-olefin, preferably ethylene, butene, hexene, octene, decene, dodecene, preferably ethylene, butene, hexene, octene).

In a preferred embodiment, the monomer is ethylene and the comonomer is hexene, preferably from 1 to 15 mole % hexene, alternately 1 to 10 mole %.

Typically, the polymers produced herein have an Mw of 5,000 to 3,000,000 g/mol (alternately 25,000 to 2,000,000 g/mol, alternately 50,000 to 1,500,000 g/mol, alternately 500,000 to 1,000,000 g/mol).

Typically, the polymers produced herein have an Mw/Mn of greater than 1 to 40 (alternately 1.2 to 20, alternately 1.3 to 10, alternately 1.4 to 5, alternately 1.5 to 4, alternately 1.5 to 3).

The polymer produced herein may have a unimodal or a multimodal molecular weight distribution as determined by Gel Permeation Chromatography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versus).

Unless otherwise indicated and for purposes of the claims to this invention Mw, Mn, and MWD are determined by GPC as described below for samples 17 and 18.

Blends

In another embodiment, the polymer (preferably the polyethylene or polypropylene) produced herein is combined with one or more additional polymers prior to being formed into a film, molded part or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In a preferred embodiment, the polymer (preferably the polyethylene or polypropylene) is present in the above blends, at from 10 to 99 wt %, based upon the weight of the polymers in the blend, preferably 20 to 95 wt %, even more preferably at least 30 to 90 wt %, even more preferably at least 40 to 90 wt %, even more preferably at least 50 to 90 wt %, even more preferably at least 60 to 90 wt %, even more preferably at least 70 to 90 wt %.

The blends described above may be produced by mixing the polymers of the invention with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

Films

Any of the foregoing polymers may be used in a variety of end-use applications. Such applications include, for example, mono- or multi-layer blown, extruded, and/or shrink films. These films may be formed by any number of well known extrusion or coextrusion techniques, such as a blown bubble film processing technique, wherein the composition can be extruded in a molten state through an annular die and then expanded to form a uni-axial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxially orientation can be accomplished using typical cold drawing or hot drawing methods. Biaxial orientation can be accomplished using tenter frame equipment or double bubble processes and may occur before or after the individual layers are brought together. For example, a polyethylene layer can be extrusion coated or laminated onto an oriented polypropylene layer or the polyethylene and polypropylene can be coextruded together into a film, then oriented. Likewise, oriented polypropylene could be laminated to oriented polyethylene or oriented polyethylene could be coated onto polypropylene, then optionally, the combination could be oriented even further. Typically, the films are oriented in the Machine Direction (MD) at a ratio of up to 15, preferably between 5 and 7, and in the Transverse Direction (TD) at a ratio of up to 15, preferably 7 to 9. However, in another embodiment, the film is oriented to the same extent in both the MD and TD directions.

The films may vary in thickness depending on the intended application; however, films of a thickness from 1 to 50 μm are usually suitable. Films intended for packaging are usually from 10 to 50 μm thick. The thickness of the sealing layer is typically 0.2 to 50 μm. There may be a sealing layer on both the inner and outer surfaces of the film or the sealing layer may be present on only the inner or the outer surface.

In another embodiment, one or more layers may be modified by corona treatment, electron beam irradiation, gamma irradiation, flame treatment, or microwave. In a preferred embodiment, one or both of the surface layers is modified by corona treatment.

In another embodiment, this invention relates to:
1. A catalyst system comprising activator, optional support, and catalyst compound represented by Formula I where Formula I is:

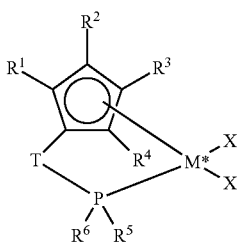

wherein:
T is a bridging group; z is 0 or 1; P is nitrogen; M* is Cr, Mo, or W; each X, is independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, including that two X's may form a part of a fused ring or a ring system;
each $R^1$, $R^2$, $R^3$, and $R^4$ is independently, hydrogen, a $C_1$ to $C_{12}$ hydrocarbyl, a substituted $C_1$ to $C_{12}$ hydrocarbyl, a heteroatom, or substituted heteroatom group; and
each $R^5$ and $R^6$ is, independently, a $C_1$ to $C_{12}$ hydrocarbyl, a substituted $C_1$ to $C_{12}$ hydrocarbyl, a heteroatom, or substituted heteroatom group, where the $R^5$ and $R^6$ groups may form a fused ring or multicenter fused ring system where the rings may be aromatic, partially saturated or saturated.

2. The catalyst system of paragraph 1 wherein M* is Cr.
3. The catalyst system of paragraph 1 or 2 wherein each $R^1$, $R^2$, $R^3$, and $R^4$ is, independently, hydrogen, methyl, ethyl, propyl, butyl, pentyl, hexyl, heptyl, octyl, nonyl, decyl, undecyl, docecyl, or an isomer thereof, Cl, Br, F, I, or Si, preferably methyl, ethyl, propyl, butyl or an isomer thereof.
4. The catalyst system of paragraph 1, 2 or 3 wherein the $P(R^5)(R^6)$ fragment is a neutral donor ligand.
5. The catalyst system of any of paragraphs 1 to 4 wherein the $P(R^5)(R^6)$ fragment is selected from the group consisting of diethylphosphino, diphenylphosphino, di-t-butylphosphino, dicyclohexylphosphino, di-p-tolylphosphino, and substituted analogs thereof, preferably where the substitutent is one or more of alkyl, aryl, silyl, or halide groups.
6. The catalyst system of any of paragraphs 1 to 5 wherein each $R^5$ and $R^6$, is, independently, methyl, ethyl, propyl, butyl, pentyl, hexyl, heptyl, octyl, nonyl, decyl, undecyl, docecyl, or an isomer thereof, or Cl, Br, F, I, or Si; and each $R^1$, $R^2$, $R^3$, $R^4$, $R^8$, $R^9$, $R^{10}$, and $R^{11}$ is, independently, selected from the group consisting of hydrogen, methyl, ethyl, propyl, butyl, pentyl, hexyl, heptyl, octyl, nonyl, decyl, undecyl, docecyl, or an isomer thereof, Cl, Br, R, I and Si.
7. The catalyst system of any of paragraphs 1 to 6 wherein each X is independently selected from chloride, bromide, methyl, ethyl, propyl, butyl and pentyl.
8. The catalyst system of any of paragraphs 1 to 7 wherein T is represented by the formula, $(R^*_2G)_g$, where each G is C, Si, or Ge, g is 1 or 2, and each $R^*$ is, independently, hydrogen, halogen, $C_1$ to $C_{20}$ hydrocarbyl or a $C_1$ to $C_{20}$ substituted hydrocarbyl, and two or more $R^*$ can form a cyclic structure including aromatic, partially saturated, or saturated cyclic or fused ring system.
9. The catalyst system of any of paragraphs 1 to 8, wherein the compound represented by Formula I comprises one or more of: tetramethyl(diethylphosphinodimethylsilyl)cyclopentadienylchromium(III) dichloride, tetramethyl(diphenylphosphinodimethylsilyl)cyclopentadienylchromium(III) dichloride, tetramethyl(di-p-tolylphosphinodimethylsilyl)cyclopentadienylchromium(III) dichloride, tetramethyl(dicyclohexylphosphinodimethylsilyl)cyclopentadienylchromium(III) dichloride, and tetramethyl(di-t-butylphosphinodimethylsilyl)cyclopentadienylchromium(III) dichloride.
10. The catalyst system of any of paragraphs 1 to 9, wherein the support is silica.
11. A process to polymerize olefins comprising contacting one or more olefins with the catalyst system of any of paragraphs 1 to 10.
12. The process of paragraph 11 wherein the activator comprises alumoxane.

13. The process of paragraph 11 or 12 wherein alumoxane is present at a molar ratio of aluminum to catalyst compound transition metal of 10:1 or more, alternately 20:1 or more, alternately 100:1 or more.
14. The process of any of paragraphs 11 to 13 wherein the activator comprises a non-coordinating anion activator.
15. The process of any of paragraphs 11 to 14 wherein the activator is represented by the formula:

$$(Z)_d^+(A^{d-})$$

wherein Z is (L-H) or a reducible Lewis Acid, L is an neutral Lewis base; H is hydrogen; (L-H)$^+$ is a Bronsted acid; A$^{d-}$ is a non-coordinating anion having the charge d−; and d is an integer from 1 to 3.
16. The process of any of paragraphs 11 to 14 wherein the activator is represented by the formula:

$$(Z)_d^+(A^{d-})$$

wherein A$^{d-}$ is a non-coordinating anion having the charge d−; d is an integer from 1 to 3, and Z is a reducible Lewis acid represented by the formula: (Ar$_3$C$^+$), where Ar is aryl or aryl substituted with a heteroatom, a C$_1$ to C$_{40}$ hydrocarbyl, or a substituted C$_1$ to C$_{40}$ hydrocarbyl.
17. The process of any of paragraphs 11 to 14 wherein the activator is one or more of: N,N-dimethylanilinium tetrakis(pentafluorophenyl)borate, triphenylcarbenium tetrakis(pentafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, [4-t-butyl-PhNMe$_2$H][(C$_6$F$_3$(C$_6$F$_5$)$_2$)$_4$B], trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate, triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium)tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl) ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, di-(i-propyl)ammonium tetrakis(pentafluorophenyl)borate, dicyclohexylammonium tetrakis(pentafluorophenyl)borate, tri(o-tolyl)phosphonium tetrakis(pentafluorophenyl)borate, tri(2,6-dimethylphenyl)phosphonium tetrakis(pentafluorophenyl)borate, triphenylcarbenium tetrakis(perfluorophenyl)borate, 1-(4-(tris(pentafluorophenyl)borate)-2,3,5,6-tetrafluorophenyl)pyrrolidinium, tetrakis(pentafluorophenyl)borate, 4-(tris(pentafluorophenyl)borate)-2,3,5,6-tetrafluoropyridine, and triphenylcarbenium tetrakis(3,5-bis(trifluoromethyl)phenyl)borate).
18. The process of any of paragraphs 11 to 17 wherein the process occurs at a temperature of from about 0° C. to about 300° C., at a pressure in the range of from about 0.35 MPa to about 10 MPa, and at a time up to 300 minutes.
19. The process of any of paragraphs 11 to 18 further comprising obtaining polymer.
20. The process of any of paragraphs 11 to 19 wherein the olefins comprise ethylene.
21. The process of any of paragraphs 11 to 18 further comprising obtaining ethylene polymer having an Mw from 50,000 to 3,000,000 g/mol and, preferably, an ethylene content of 75 to 100 mol %, optionally 80 to 100 mol %.

EXPERIMENTAL

MAO is methyl alumoxane (30 wt % in toluene) obtained from Albemarle.

Room temperature is 23° C. unless otherwise noted.

Examples Catalyst Synthesis

Example 1

Tetramethyl(diphenylphosphinodimethylsilyl)cyclopentadiene

In 50 mL of tetrahydrofuran (THF) was dissolved 3.84 mL (22.1 mmol) of diphenylphosphine. To this solution was added 8.25 mL of a 2.67 M solution of n-butyllithium in hexanes (22.0 mmol). The resultant solution was stirred at room temperature for 1 hour. It was then chilled to −30° C. A solution of 4.74 g (22.1 mmol) of tetramethyl(chlorodimethylsilyl)cyclopentadiene dissolved in 10 mL of THF was added dropwise. The reaction mixture was allowed to warm to room temperature with stirring overnight. The reaction mixture was then stripped of solvent in vacuo, and the residue left behind was extracted into pentane. This mixture was filtered through Celite™, and the filtrate was subsequently stripped of solvent, leaving 7.85 g of the desired compound. $^1$H NMR ($C_6D_6$, ppm): 7.54 (m, 4H); 7.08 (m, 6H); 2.95 (br s, 1H); 2.02 (s, 6H); 1.76 (s, 6H); 0.13 (d, 6H).

Example 2

Tetramethyl(diphenylphosphinodimethylsilyl)cyclopentadienylchromium(III) chloride In 150 mL of THF was dissolved 7.85 g (21.5 mmol) of tetramethyl(diphenylphosphinodimethylsilyl)cyclopentadiene. To this solution was added 8.05 mL of a 2.67 M solution of n-butyllithium in hexanes (21.5 mmol). The resultant solution was stirred at room temperature for 1 hour. It was then chilled to −30° C. To this solution, 8.07 g (21.5 mmol) of $CrCl_3(THF)_3$ was added as a solid. The reaction mixture was then allowed to warm to room temperature with stirring overnight. The reaction mixture was then dried, and the residue was dissolved in toluene. The mixture was filtered through Celite™, using methylene chloride to assist in the filtration. The filtrate was brought to dryness, and subsequently crystallized from a methylene chloride/pentane mixture, yielding 0.54 g of the desired compound.

Example 3

Supported Tetramethyl(diphenylphosphinodimethylsilyl)cyclopentadienylchromium(III) chloride 948 mg of a 30% by weight solution of methylalumoxane (MAO) in toluene was diluted further with 954 mg of toluene. This solution was stirred for 15 minutes. To this solution, 19.6 mg (40.3 μmol) of tetramethyl(diphenylphosphinodimethylsilyl)cyclopentadienylchromium(III) chloride was added as a solid, and this mixture was stirred for 15 minutes. To the mixture was added 757 mg of silica (Grace-Davison™ 948 grade, calcined at 600° C.). The resultant mixture was stirred by spatula for 10 minutes. This wet mass was dried overnight in vacuo, yielding 0.873 g of finished catalyst.

Example 4

Tetramethyl(diethylphosphinodimethylsilyl)cyclopentadiene

In 80 mL of tetrahydrofuran (THF) was dissolved 5.09 g (56.5 mmol) of diethylphosphine; this solution was chilled to 0° C. To this solution was added 21.1 mL of a 2.67 M solution of n-butyllithium in hexanes (56.3 mmol). The resultant solution was stirred at 0° C. for 1 hour. A solution of 12.5 mL (56.6 mmol) of tetramethyl(chlorodimethylsilyl)cyclopentadiene dissolved in 10 mL of THF was added dropwise. The reaction mixture was allowed to warm to room temperature with stirring overnight. The reaction mixture was then stripped of solvent in vacuo, and the residue left behind was extracted into pentane. This mixture was filtered through Celite™, and the filtrate was subsequently stripped of solvent. The residue was distilled under vacuum, yielding 7.96 g of the desired compound. $^1$H NMR ($C_6D_6$, ppm): 2.86 (br s, 1H); 2.05 (s, 6H); 1.82 (s, 6H); 1.39 (m, 4H); 1.11 (m, 6H); 0.10 (d, 6H).

Example 5

Tetramethyl(diethylphosphinodimethylsilyl)cyclopentadienylchromium(III) chloride In 50 mL of THF was dissolved 1.80 g (6.69 mmol) of tetramethyl(diethylphosphinodimethylsilyl)cyclopentadiene. To this solution was added 2.50 mL of a 2.67 M solution of n-butyllithium in hexanes (6.68 mmol). The resultant solution was stirred at room temperature for 1 hour. It was then chilled to −80° C. To this solution, 2.51 g (6.69 mmol) of $CrCl_3(THF)_3$ was added as a solid. The reaction mixture was then allowed to warm to room temperature with stirring overnight. The reaction mixture was then dried, and the residue was dissolved in toluene. The mixture was filtered through Celite™, using methylene chloride to assist in the filtration. The filtrate was brought to dryness, and subsequently crystallized from a methylene chloride/toluene mixture, yielding 1.14 g of the desired compound.

Example 6

Supported Tetramethyl(diethylphosphinodimethylsilyl)cyclopentadienylchromium(III) chloride 949 mg of a 30% by weight solution of methylalumoxane (MAO) in toluene was diluted further with 1 mL of toluene. This solution was stirred for 15 minutes. To this solution, 15.9 mg (40.7 μmol) of tetramethyl(diethylphosphinodimethylsilyl)cyclopentadienylchromium(III) chloride was added as a solid, and this mixture was stirred for 15 minutes. To the mixture was added 763 mg of silica (Grace-Davison™ 948 grade, calcined at 600° C.). The resultant mixture was stirred by spatula for 10 minutes. This wet mass was dried overnight in vacuo, yielding 1.02 g of finished catalyst.

Example 7

Tetramethyl(dicyclohexylphosphinodimethylsilyl)cyclopentadiene

In 100 mL of ether was dissolved 0.89 mL (4.06 mmol) of dicyclohexylphosphine. To this solution was added 1.51 mL of a 2.67 M solution of n-butyllithium in hexanes (4.03 mmol). The resultant solution was stirred at room temperature for 1 hour. A solution of 1.33 g (4.04 mmol) of tetramethyl(triflatodimethylsilyl)cyclopentadiene dissolved in 5 mL of ether was added dropwise. The reaction mixture was allowed to stir overnight. The reaction mixture was then stripped of solvent in vacuo, and the residue left behind was extracted into pentane. This mixture was filtered through Celite™, and the filtrate was subsequently stripped of solvent, yielding 1.44 g of the desired compound. $^1$H NMR ($C_6D_6$, ppm): 2.99 (br s, 1H); 2.13 (s, 6H); 1.18-1.95 (m, 28H); 0.26 (d, 6H).

Example 8

Tetramethyl(dicyclohexylphosphinodimethylsilyl) cyclopentadienylchromium(III) chloride In 60 mL of THF was dissolved 1.44 g (3.83 mmol) of tetramethyl(dicyclohexylphosphinodimethylsilyl)cyclopentadiene. To this solution was added 1.43 mL of a 2.67 M solution of n-butyllithium in hexanes (3.82 mmol). The resultant solution was stirred at room temperature for 1 hour. It was then chilled to −80° C. To this solution, 1.43 g (3.83 mmol) of $CrCl_3(THF)_3$ was added as a solid. The reaction mixture was then allowed to warm to room temperature with stirring overnight. The reaction mixture was then dried, and the residue was dissolved in toluene. The mixture was filtered through Celite™, using methylene chloride to assist in the filtration. The filtrate was brought to dryness, and subsequently crystallized from a methylene chloride/toluene mixture, yielding 299.6 mg of the desired compound.

Example 9

Tetramethyl(di-p-tolylphosphinodimethylsilyl)cyclopentadiene

In 125 mL of tetrahydrofuran (THF) was dissolved 4.51 g (21 0 mmol) of d-p-tolylphosphine. To this solution was added 7.9 mL of a 2.67 M solution of n-butyllithium in hexanes (21 mmol). The resultant solution was stirred at room temperature for 1 hour. The solution was then chilled to −30° C. 4.65 mL (21.0 mmol) of tetramethyl(chlorodimethylsilyl)cyclopentadiene was added dropwise. The reaction mixture was allowed to stir overnight. The reaction mixture was then stripped of solvent in vacuo, and the residue left behind was extracted into pentane. This mixture was filtered through Celite™, and the filtrate was subsequently stripped of solvent. The residue was distilled under vacuum, yielding 2.11 g of the desired compound. $^1$H NMR ($C_6D_6$, ppm): 7.53 (t, 4H); 6.95 (d, 4H); 3.02 (br s, 1H); 2.07 (s, 12H); 1.79 (s, 6H); 0.18 (d, 6H).

Example 10

Tetramethyl(di-p-tolylphosphinodimethylsilyl)cyclopentadienylchromium(III) chloride In 125 mL of THF was dissolved 2.11 g (5.39 mmol) of tetramethyl(di-p-tolylphosphinodimethylsilyl)cyclopentadiene. To this solution was added 2.02 mL of a 2.67 M solution of n-butyllithium in hexanes (5.39 mmol). The resultant solution was stirred at room temperature for 1 hour. It was then chilled to −80° C. To this solution, 2.02 g (5.39 mmol) of $CrCl_3(THF)_3$ was added as a solid. The reaction mixture was then allowed to warm to room temperature with stirring overnight. The reaction mixture was then dried, and the residue was dissolved in toluene. The mixture was filtered through Celite™. The filtrate was brought to dryness, and subsequently crystallized from toluene, yielding 0.769 g of the desired compound.

Example 11

Tetramethyl(di-t-butylphosphinodimethylsilyl)cyclopentadiene

In 125 mL of tetrahydrofuran (THF) was dissolved 1.16 mL (6.27 mmol) of di-t-butylphosphine. To this solution was added 2.34 mL of a 2.67 M solution of n-butyllithium in hexanes (6.25 mmol). The resultant solution was stirred at room temperature for 1.5 hours, and then chilled to −40° C. A solution of 2.06 g (6.27 mmol) of tetramethyl(triflatodimethylsilyl)cyclopentadiene dissolved in 5 mL of THF was added dropwise. The reaction mixture was allowed to warm to room temperature with stirring overnight. The reaction mixture was then stripped of solvent in vacuo, and the residue left behind was extracted into pentane. This mixture was filtered through Celite, and the filtrate was subsequently stripped of solvent. The residue was distilled under vacuum, yielding 2.21 g of the desired compound. $^1$H NMR ($C_6D_6$, ppm): 3.21 (br s, 1H); 2.15 (s, 6H); 1.84 (s, 6H); 1.32 (d, 18H); 0.23 (d, 6H).

Example 12

Tetramethyl(di-t-butylphosphinodimethylsilyl)cyclopentadienylchromium(III) chloride In 50 mL of THF was dissolved 0.982 g (3.03 mmol) of tetramethyl(di-t-butylphosphinodimethylsilyl)cyclopentadiene. To this solution was added 1.13 mL of a 2.67 M solution of n-butyllithium in hexanes (3.02 mmol). The resultant solution was stirred at room temperature for 1 hour. It was then chilled to −40° C. To this solution, 1.11 g (2.97 mmol) of $CrCl_3(THF)_3$ was added as a solid. The reaction mixture was then allowed to warm to room temperature with stirring overnight. The reaction mixture was then dried, and the residue was dissolved in toluene. The mixture was filtered through Celite™. The filtrate was brought to dryness, and subsequently crystallized from toluene, yielding 142 mg of the desired compound.

Experimental—Polymerizations

Conversion factors: 1 psi equals 6.894757 kPa and 1 atm equals 101.325 kPa.

Solvents, polymerization grade toluene, and hexanes were supplied by ExxonMobil Chemical Company and thoroughly dried and degassed prior to use.

The following conditions apply to examples 13 through 16: polymerization grade ethylene was used and further purified by passing it through a series of columns: 500 cc Oxyclear cylinder from Labclear (Oakland, Calif.) followed by a 500 cc column packed with dried 3 Å mole sieves purchased from Aldrich Chemical Company, and a 500 cc column packed with dried 5 Å mole sieves purchased from Aldrich Chemical Company.

TnOAl (tri-n-octylaluminum, neat) was used as a 2 mmol/L solution in toluene.

Reactor Description and Preparation: Polymerizations were conducted in an inert atmosphere ($N_2$) drybox using autoclaves equipped with an external heater for temperature control, glass inserts (internal volume of reactor=22.5 mL), septum inlets, regulated supply of nitrogen, ethylene and propylene, and equipped with disposable PEEK mechanical stirrers (800 rpm). The autoclaves were prepared by purging with dry nitrogen prior to use.

Ethylene/1-hexene Copolymerization

The reactor was prepared as described above, and then purged with ethylene. Isohexane, 1-hexene, and MAO were added via syringe at room temperature and atmospheric pressure. The reactor was then brought to process temperature (80° C. or 105° C.) and charged with ethylene to process pressure (75 psig=896 kPa or 110 psig=758 kPa) while stirring at 800 rpm. The transition metal compound "TMC" (150 µL of a 200 µM toluene solution, unless indicated otherwise) was added via syringe with the reactor at process conditions. MAO was used as 48.3 µL of a 0.5% by mass solution in toluene. Amounts of reagents not specified above are given in Table 1. , Ethylene was allowed to enter (through the use of computer controlled solenoid valves) the autoclaves during polymerization to maintain reactor gauge pressure (+/−2 psig). Reactor temperature was monitored and typically maintained within +/−1° C. Polymerizations were halted by addition of approximately 175 psi $O_2$/Ar (5 mole % $O_2$) gas mixture to the autoclaves for approximately 30 seconds. The polymerizations were quenched after a predetermined cumulative amount of ethylene had been added or for a maximum of 20 minutes polymerization time. The final conversion (in psi) of ethylene added/consumed is reported in Table 1, in addition to the quench time for each run. The reactors were cooled and vented. The polymer was isolated after the solvent was removed in-vacuo. Yields reported include total weight of polymer and residual catalyst. Catalyst activity is reported as grams of polymer per mmol transition metal compound per atmosphere ethylene per hour of reaction time (g/mmol·r·atm).

Examples 17 and 18 were run under the following conditions:

A 2 liter zipper autoclave reactor was heated to 130° C. using a steam/water mix, and nitrogen was flowed through for 90 minutes. It was then charged with 700 mL of isohexane and 30 mL of 1-hexene, as well as a 2 mL solution of tri-n-octylaluminum dissolved in hexane (0.11 M). The reactor was brought to process temperature (80° C.) and charged with ethylene to process pressure. The supported catalyst was then injected into the reactor using ethylene, and the polymerization reaction was allowed to run for 60 minutes, with stirring being maintained at 500 rpm. Temperature was maintained +/−2° C. by the steam/water conduit, and pressure was maintained +/−2 psig by a computer-controlled mass-flow controller and a regulator set to 180 psig. After 60 minutes, the reactor was allowed to cool to 50° C., vented, and the solvent removed, and the yield was determined Polymer Characterization:

For examples 13 through 16, polymer characterization results for polyethylene samples are reported in Table 2. , For analytical testing, polymer sample solutions were prepared by dissolving polymer in 1,2,4-trichlorobenzene (TCB, 99+% purity from Sigma-Aldrich) containing 2,6-di-tert-butyl-4-methylphenol (BHT, 99% from Aldrich) at 160° C. in a shaker oven for approximately 3 hours. The typical concentration of polymer in solution is between 0.4 to 0.9 mg/mL with a BHT concentration of 1.25 mg BHT/mL of TCB. Samples are cooled to 135° C. for testing.

Molecular weights (weight average molecular weight (Mw) and number average molecular weight (Mn)) and molecular weight distribution (MWD=Mw/Mn), which is also sometimes referred to as the polydispersity (PDI) of the polymer, were measured by Gel Permeation Chromatography using a Symyx Technology GPC equipped with evaporative light scattering detector and calibrated using polystyrene standards (Polymer Laboratories: Polystyrene Calibration Kit S-M-10: Mp (peak Mw) between 5000 and 3,390,000). Samples were run in TCB at (135° C. sample temperatures, 160° C. oven/columns) using three Polymer Laboratories: PLgel 10 µm Mixed-B 300×7.5 mm columns in series. No column spreading corrections were employed. Numerical analyses were performed using Epoch® software available from Symyx Technologies.

The sample preparation for SAMMS (Sensory Array Modular Measurement System) thermal analysis measurements involved depositing the stabilized polymer solution onto a silanized wafer (Part Number S10457, Symyx). The solvent was then evaporated off at ~145° C. By this method, approximately between 0.12 and 0.24 mg of polymer is deposited onto each corresponding wafer cell. Thermal analysis was measured on a Symyx Technologies SAMMS instrument that measures polymer melt temperatures via the 3 ω technique. The analysis first employs a rapid-scan protocol that heats each cell from 27° C. to 200° C. in ~35 seconds and then rapidly cools the sample to room temperature. This complete procedure takes approximately 60 seconds per cell and is used to minimize each sample's thermal history. The second step involves running a high-resolution scan protocol to measure the second melt of the sample. The protocol heats each cell from 27° C. to 200° C. in ~3 minutes and then rapidly cools the sample to room temperature. The high-resolution scan takes approximately three times the amount of time to complete as the rapid-scan protocol. If multiple melting peaks are present, Epoch® Software reports the largest amplitude peak. SAMMS data is reported under the heading of Tm (° C.).

Samples for infrared analysis were prepared by depositing the stabilized polymer solution onto a silanized wafer (Part number S10860, Symyx). By this method, approximately between 0.12 and 0.24 mg of polymer is deposited on the wafer cell. The samples were subsequently analyzed on a Brucker Equinox 55 FTIR spectrometer equipped with Pike's MappIR specular reflectance sample accessory. Spectra, covering a spectral range of 5000 $cm^{-1}$ to 500 $cm^{-1}$, were collected at a 2 $cm^{-1}$ resolution with 32 scans.

For samples 17 and 18, characterization was performed as follows: gel permeation chromatography was performed on a Waters Alliance GPC 2000 or a PL GPC 220 (Agilent Technologies) equipped with a differential refractive index (DRI) detector. The solvent consisted of 1,2,4-trichlorobenzene (Sigma Aldrich, Chromasolv grade≥99% purity) stabilized with 1000 ppm of 2,6-di-tert-butyl-4-methylphenol (Sigma Aldrich) and was filtered using a membrane filter (Millipore, polytetrafluoroethylene, 0.1 µm). All samples were dissolved at a concentration of approximately 0.5 to 1.5 mg/mL in this solvent. Dissolution was carried out at 160° C. in a shaker oven for 2-3 hours. The samples were immediately transferred to sample carousel maintained at 145° C. (Waters Alliance GPC 2000) or the auto-sampler maintained at 150-160° C. (PL GPC 200). Separation was effected by three Mixed B columns in series (Agilent Technologies, PL-Gel 10 µm 300 mm×5 mm) at 145° C. (Waters Alliance GPC 2000) or 160° C. (PL GPC 200). The solvent was passed through an in-line filter (Optimize Technologies, SS frit, 2 µm) prior to entering the columns at a fixed flow rate of 1.0 mL/min Molecular weight was determined by a conventional calibration as described below using a set of seventeen narrow polystyrene standards (Agilent Technologies) with peak molecular weights (Mp) from ~1000 to ~10,000,000 g/mol and Mw/Mn≤1.10. MP for the polystyrene standard provided on the certificate of analysis from the manufacturer acquired through independent characterization by viscometry and light scattering was used for calibration. The conventional calibration curve was generated by fitting a second order polynomial to a plot of the log Mp vs. retention volume for the polystyrene standards in Microsoft Excel (Version 14.0.7113.5000). Using this calibration and the Mark-Houwink expression, molecular weight moments were determined for polyolefins of known composition. The composition used for GPC analysis was determined by $^1$H NMR.

Polymer composition was determined by $^1$H NMR using a Varian DD2 500 MHz instrument run with a 30° flip angle RF pulse, 120 scans, with a delay of 5 seconds between to pulses. The polymer sample was dissolved in heated $d_2$-1,1,2,2-tetrachloroethane and signal collection took place at 120° C. Number of Methyl Groups/1000 Carbons=(MRA/3)*1000)/RIA/2)] where: MRA: Methyl region area between 0.85 and 1.05 ppm and IA: Integration area between 0 and 2.1 ppm.

TABLE 1

Unsupported Catalyst - Ethylene-hexene copolymerization runs

| Ex # | Catalyst Example | Catalyst amount (μmol) | Temp (° C.) | Pressure (psi) | Total Isohexane (mL) | 1-hexene (μL) | Final Conversion (psi) | Quench Time (sec) | Polymer Yield (mg) | Activity (g/mmol · atm · hr) | Runs averaged |
|---|---|---|---|---|---|---|---|---|---|---|---|
| 13 | 5 | 0.03 | 80 | 75 | 5 | 100 | 15.1 | 420 | 25.6 | 1434 | 4 |
| 14 | 8 | 0.03 | 80 | 75 | 5 | 100 | 15.2 | 177 | 28.5 | 3789 | 3 |
| 15 | 8 | 0.03 | 105 | 110 | 5 | 100 | 5.2 | 600 | 13.7 | 366 | 4 |
| 16 | 12 | 0.03 | 80 | 75 | 5 | 100 | 10.3 | 600 | 12.9 | 506 | 4 |

TABLE 2

Unsupported Catalyst - Ethylene-hexene copolymerization runs (cont'd)

| Ex # | Mw (g/mol) | Mn (g/mol) | Mw/Mn | Tm (° C.) | hexene content (wt %) |
|---|---|---|---|---|---|
| 13 | 10,400 | 5,800 | 1.79 | 118.0 | 24.4 |
| 14 | 260,000 | 147,000 | 1.77 | 125.8 | 3.2 |
| 15 | 71,300 | 42,700 | 1.67 | 125.5 | 6.5 |
| 16 | 250,000 | 33,000 | 7.58 | 129.4 | 1.46 |

TABLE 3

Supported catalyst - Ethylene hexene runs

| Example | Catalyst example | Pressure (psi) | Uptake (g) | Polymer yield (g) | Activity (g/g · atm · hr) |
|---|---|---|---|---|---|
| 17* | 3 | 190 | 6.2 | 1.0 | 2 |
| 18 | 6 | 180 | 21.2 | 14.4 | 23 |

*average of three runs

TABLE 4

Supported catalyst - Ethylene hexene runs (cont'd)

| Example | Catalyst example | Mn (g/mol) | Mw (g/mol) | Mw/Mn | Hexene content (wt %) |
|---|---|---|---|---|---|
| 17 | 3 | 44,000 | 302,000 | 6.9 | 18 |
| 18 | 6 | 3,300 | 126,000 | 38 | 2.5 |

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise whenever a composition, an element or a group of elements is preceded with the transitional phrase "comprising", it is understood that we also contemplate the same composition or group of elements with transitional phrases "consisting essentially of," "consisting of", "selected from the group consisting of," or "is" preceding the recitation of the composition, element, or elements and vice versa.

What is claimed is:

1. A catalyst system for the polymerization of ethylene and alpha-olefin comprising activator, catalyst compound, and support where the catalyst compound is represented by Formula I:

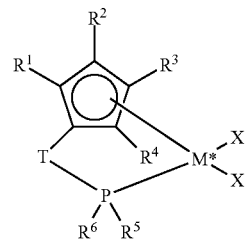

where
T is a bridging group represented by the formula, $(R^*_2G)_g$, where each G is Si or Ge, g is 1, and each $R^*$ is, independently, hydrogen, halogen, $C_1$ to $C_{20}$ hydrocarbyl or a $C_1$ to $C_{20}$ substituted hydrocarbyl, and two or more R* optionally form a cyclic structure including a saturated cyclic or fused ring system; P is phosphorus; M* is Cr, Mo, or W; each X, is independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, including that two X's optionally form a part of a fused ring or a ring system;

each $R^1$, $R^2$, $R^3$, and $R^4$ is independently, hydrogen, a $C_1$ to $C_{12}$ hydrocarbyl, a substituted $C_1$ to $C_{12}$ hydrocarbyl, a heteroatom, or substituted heteroatom group; and each $R^5$ and $R^6$ is, independently, a $C_1$ to $C_{12}$ hydrocarbyl, a substituted $C_1$ to $C_{12}$ hydrocarbyl, a heteroatom, or substituted heteroatom group, where the $R^5$ and $R^6$ groups optionally form a fused ring or multicenter fused ring system where the rings may be aromatic, partially saturated or saturated.

2. The catalyst system of claim 1, wherein M* is Cr.

3. The catalyst system of claim 1, wherein each $R^1$, $R^2$, $R^3$, and $R^4$ is, independently, hydrogen, methyl, ethyl, propyl, butyl, pentyl, hexyl, heptyl, octyl, nonyl, decyl, undecyl, docecyl, or an isomer thereof, Cl, Br, F, or I.

4. The catalyst system of claim 1, wherein the $P(R^5)(R^6)$ fragment is a neutral donor ligand.

5. The catalyst system of claim 1, wherein the $P(R^5)(R^6)$ fragment is selected from the group consisting of diethylphosphino, diphenylphosphino, di-t-butylphosphino, dicyclohexylphosphino, di-p-tolylphosphino, and substituted analogs thereof.

6. The catalyst system of claim 1, wherein each $R^5$ and $R^6$, is, independently, methyl, ethyl, propyl, butyl, pentyl, hexyl, heptyl, octyl, nonyl, decyl, undecyl, docecyl, or an isomer thereof, or Cl, Br, F, I or Si; and each $R^1$, $R^2$, $R^3$, and $R^4$ is, independently, selected from the group consisting of hydrogen, methyl, ethyl, propyl, butyl, pentyl, hexyl, heptyl, octyl, nonyl, decyl, undecyl, docecyl, or an isomer thereof, Cl, F, I, or Br.

7. The catalyst system of claim 1, wherein each X is independently selected from chloride, bromide, methyl, ethyl, propyl, butyl and pentyl.

8. The catalyst system of claim 1, wherein each R* is, independently, $C_1$ to $C_{20}$ hydrocarbyl or a $C_1$ to $C_{20}$ substituted hydrocarbyl.

9. A catalyst system for the polymerization of ethylene and alpha-olefin comprising activator, catalyst compound, and support where the catalyst compound:
   comprises one or more of:
   tetramethyl(diethylphosphinodimethylsilyl)cyclopentadienylchromium(III) dichloride,
   tetramethyl(diphenylphosphinodimethylsilyl)cyclopentadienylchromium(III) dichloride,
   tetramethyl(di-p-tolylphosphinodimethylsilyl)cyclopentadienylchromium(III) dichloride,
   tetramethyl(dicyclohexylphosphinodimethylsilyl)cyclopentadienylchromium(III) dichloride, and
   tetramethyl(di-t-butylphosphinodimethylsilyl)cyclopentadienylchromium(III) dichloride.

10. A catalyst system for the polymerization of ethylene and alpha-olefin comprising activator, catalyst compound, and a support where the catalyst compound is represented by Formula I:

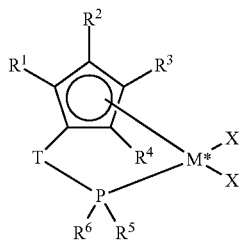

where
T is a bridging group represented by the formula, $(R^*_2G)_g$, where each G is C, Si, or Ge, g is 1, and each R* is, independently, hydrogen, halogen, $C_1$ to $C_{20}$ hydrocarbyl or a $C_1$ to $C_{20}$ substituted hydrocarbyl, and two or more R* optionally form a cyclic structure including a saturated cyclic or fused ring system; P is phosphorus; M* is Cr, Mo, or W; each X, is independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, including that two X's optionally form a part of a fused ring or a ring system;
each $R_1$, $R^2$, $R^3$, and $R^4$ is independently, hydrogen, a $C_1$ to $C_{12}$ hydrocarbyl, a substituted $C_1$ to $C_{12}$ hydrocarbyl, a heteroatom, or substituted heteroatom group; and
each $R^5$ and $R^6$ is, independently, a $C_1$ to $C_{12}$ hydrocarbyl, a substituted $C_1$ to $C_{12}$ hydrocarbyl, a heteroatom, or substituted heteroatom group, where the $R^5$ and $R^6$ groups optionally form a fused ring or multicenter fused ring system where the rings are aromatic, partially saturated or saturated, and
the support is silica.

11. The catalyst system of claim 10, wherein M* is Cr.

12. The catalyst system of claim 10, wherein each $R^1$, $R^2$, $R^3$, and $R^4$ is, independently, hydrogen, methyl, ethyl, propyl, butyl, pentyl, hexyl, heptyl, octyl, nonyl, decyl, undecyl, docecyl, or an isomer thereof, Cl, Br, F, or I.

13. The catalyst system of claim 10, wherein the $P(R^5)(R^6)$ fragment is a neutral donor ligand.

14. The catalyst system of claim 10, wherein the $P(R^5)(R^6)$ fragment is selected from the group consisting of diethylphosphino, diphenylphosphino, di-t-butylphosphino, dicyclohexylphosphino, di-p-tolylphosphino, and substituted analogs thereof.

15. The catalyst system of claim 10, wherein each $R^5$ and $R^6$, is, independently, methyl, ethyl, propyl, butyl, pentyl, hexyl, heptyl, octyl, nonyl, decyl, undecyl, docecyl, or an isomer thereof, or Cl, Br, F, I or Si; and each $R^1$, $R^2$, $R^3$, and $R^4$ is, independently, selected from the group consisting of hydrogen, methyl, ethyl, propyl, butyl, pentyl, hexyl, heptyl, octyl, nonyl, decyl, undecyl, docecyl, or an isomer thereof, Cl, F, I, or Br.

16. The catalyst system of claim 10, wherein each X is independently selected from chloride, bromide, methyl, ethyl, propyl, butyl and pentyl.

17. The catalyst system of claim 10, wherein T is $CH_2$, $C(CH_3)_2$, $SiMe_2$, $SiPh_2$, $SiMePh$, $Si(CH_2)_3$, $Si(CH_2)_4$, $Si(CH_2)_5$, or $CPh_2$.

18. The catalyst system of claim 10, wherein G is Si, g is 1 and each R* is, independently, hydrogen, halogen, $C_1$ to $C_{20}$ hydrocarbyl or a $C_1$ to $C_{20}$ substituted hydrocarbyl.

19. The catalyst system of claim 1, wherein T is a bridging group represented by the formula, $R^*_2Si$, where each R* is, independently, hydrogen, halogen, $C_1$ to $C_{20}$ hydrocarbyl or a $C_1$ to $C_{20}$ substituted hydrocarbyl, and two or more R* optionally form a cyclic structure including a saturated cyclic or fused ring system; P is phosphorus; M* is Cr; each X, is independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, including that two X's optionally form a part of a fused ring or a ring system;
each $R^1$, $R^2$, $R^3$, and $R^4$ is independently, hydrogen, a $C_1$ to $C_{12}$ hydrocarbyl, a substituted $C_1$ to $C_{12}$ hydrocarbyl, a heteroatom, or substituted heteroatom group; and
each $R^5$ and $R^6$ is, independently, a $C_1$ to $C_{12}$ hydrocarbyl, a substituted $C_1$ to $C_{12}$ hydrocarbyl, a heteroatom, or substituted heteroatom group, where the $R^5$ and $R^6$ groups optionally form a fused ring or multicenter fused ring system where the rings may be aromatic, partially saturated or saturated.

* * * * *